United States Patent
Hayashi et al.

(10) Patent No.: US 8,506,750 B2
(45) Date of Patent: Aug. 13, 2013

(54) COMPOSITE STRUCTURE AND PROCESS FOR PRODUCING THE SAME

(75) Inventors: Fumihiro Hayashi, Osaka (JP); Yasuhiro Okuda, Osaka (JP); Motomi Nakata, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 722 days.

(21) Appl. No.: 12/401,219

(22) Filed: Mar. 10, 2009

(65) Prior Publication Data

US 2009/0173439 A1   Jul. 9, 2009

Related U.S. Application Data

(62) Division of application No. 10/590,739, filed as application No. PCT/JP2004/002428 on Feb. 27, 2004, now abandoned.

(51) Int. Cl.
*B32B 37/00* (2006.01)

(52) U.S. Cl.
USPC .................................. 156/308.2; 156/309.6

(58) Field of Classification Search
USPC .................................. 156/184, 308.2, 309.6
See application file for complete search history.

(56) References Cited

U.S. PATENT DOCUMENTS

| | | | | |
|---|---|---|---|---|
| 5,102,604 A * | 4/1992 | Sidles et al. | | 264/257 |
| 5,735,892 A * | 4/1998 | Myers et al. | | 623/1.13 |
| 5,749,880 A * | 5/1998 | Banas et al. | | 606/198 |
| 5,928,279 A | 7/1999 | Shannon et al. | | |
| 6,016,848 A * | 1/2000 | Egres, Jr. | | 138/137 |
| 6,165,211 A | 12/2000 | Thompson | | |
| 6,245,099 B1 | 6/2001 | Edwin et al. | | |
| 6,364,904 B1 * | 4/2002 | Smith | | 623/1.22 |
| 6,488,701 B1 * | 12/2002 | Nolting et al. | | 623/1.13 |
| 6,673,103 B1 | 1/2004 | Golds et al. | | |
| 2002/0147490 A1 | 10/2002 | Pletzer et al. | | |

FOREIGN PATENT DOCUMENTS

| | | |
|---|---|---|
| JP | 63-303699 | 12/1988 |
| JP | 7-24072 | 1/1995 |
| JP | 07-024072 | 1/1995 |
| JP | 08-141090 | 6/1996 |

(Continued)

OTHER PUBLICATIONS

International Preliminary Report on Patentability issued in International Application No. PCT/JP2004/002428, dated Nov. 30, 2006.

(Continued)

*Primary Examiner* — Jeff Aftergut
(74) *Attorney, Agent, or Firm* — McDermott Will & Emery LLP

(57) ABSTRACT

A composite structure comprising two polytetrafluoroethylene porous layers and a framework structural member having a plurality of gaps or openings, the framework structural member being disposed between the two polytetrafluoroethylene porous layers, wherein the composite structure is structured such that the polytetrafluoroethylene porous layers are united together by being adhered with each other through the gaps or openings of the framework structural member and such that the respective polytetrafluoroethylene porous layers (A1) and (A2) are united with the framework structural member closely along the surfaces of the respective constituent elements of the framework structural member in such a manner as to wrap the respective elements. The method of manufacturing the composite structure is characterized in that it includes a step of applying pressure through a mass of fine particles.

8 Claims, 8 Drawing Sheets

(56) References Cited

FOREIGN PATENT DOCUMENTS

| | | |
|---|---|---|
| JP | 10-510196 | 10/1998 |
| JP | 2000-501328 | 2/2000 |
| JP | 2000-508216 | 7/2000 |
| JP | 2001-327609 | 11/2001 |
| JP | 2002-525166 | 8/2002 |
| JP | 2003-500103 | 1/2003 |
| JP | 2003-520628 | 7/2003 |
| WO | WO 95/05132 | 2/1995 |
| WO | WO 96/28115 | 9/1996 |
| WO | WO 98/00090 | 1/1998 |
| WO | WO 98/14137 | 4/1998 |
| WO | WO 98/26731 | 6/1998 |
| WO | WO 00/18328 | 4/2000 |
| WO | WO 00/71057 A1 | 11/2000 |
| WO | WO 01/06953 A1 | 2/2001 |
| WO | WO 01/15633 | 3/2001 |

OTHER PUBLICATIONS

Japanese Office Action issued in Japanese Patent Application No. JP 2002-333725, dated Jun. 26, 2007.

European Search Report, with written opinion, issued in European Patent Application No. 04715531.2-1526 dated on Sep. 29, 3008.

* cited by examiner

Application of pressure

COMPOSITE STRUCTURE AND PROCESS FOR PRODUCING THE SAME

RELATED APPLICATIONS

This application is a Divisional of U.S. application Ser. No. 10/590,739, filed Aug. 25, 2006, now abandoned which is a U.S. National Phase under 35 U.S.C. §371 of International Application No. PCT/JP2004/002428, filed on Feb. 27, 2004, the entire contents of each of which are hereby incorporated by reference.

TECHNICAL FIELD

The present invention relates to a composite structure, and more particularly to a composite structure which is made by coating a layer of polytetrafluoroethylene porous material (hereinafter, the "PTFE porous material") on a framework structural member made of a metal wire or the like and uniting them together. The invention also relates to a method of manufacturing such composite structure. The composite structure of the present invention is suitable for a stent used for expanding a luminal part such as a blood vessel or provide a release passage inside a lumen.

BACKGROUND ART

Generally, a PTFE porous material is manufactured by an expansion method and has a micro fibrous structure consisting of very thin fibers (fibrils) and nodes connected together with the fibers. The PTFE porous material is provided with a structure and characteristics as a porous material by such a micro fibrous structure, and the pore size, the porosity, etc. can be set to the desired values by controlling the expansion conditions, etc. The PTFE porous material obtained by the expansion method is called an expanded PTFE porous material (hereinafter, occasionally referred to as "ePTFE porous material").

The PTFE porous material exhibits surface characteristics such as low coefficient of friction, water repellence, non-stickiness, etc. in addition to the characteristics such as heat resistance and chemical resistance which are inherent in polytetrafluoroethylene itself. Also, because of its porous structure, the PTFE porous material is afforded with characteristics such as flexibility, fluid permeability, property of uptaking fine particles, filtration property, low dielectric constant, low dielectric dissipation factor, etc. Since the PTFE porous material has such peculiar porous structure and characteristics, its use is expanding to the medical field in addition to the general field of industries.

For example, a tubular PTFE porous material is widely used as an artificial blood vessel for maintaining blood circulation, since it exhibits not only high flexibility and excellent antithrombogenicity that is inherent in polytetrafluoroethylene itself but also superior biocompatibility because of the porous structure based on the micro fibrous structure. That is, the artificial blood vessel made of a tubular PTFE porous material is widely used for transplantation or bypass at a lesion part of a blood vessel in a living body.

In recent years, for the purpose of decreasing the operative invasion into the human body, the method is developed in which a stent that can be delivered by a catheter and that has an elastic structure for shrinking/expanding in the radial direction is put in a blood vessel in such a manner as to expand a constricted cavity of the blood vessel. Such a stent is generally made of an elastic wire; the stent comprising an elastic wire made of metal is called a "metallic stent". A stent that can be formed by covering such a metallic stent with a PTFE porous material has been developed. Such a covered stent can be used as an artificial blood vessel, i.e., a stent-graft or a blood vessel prosthetic device, which is made by providing a framework structural member (metallic stent) made of metal and capable of radial expansion/contraction with a covering material.

If such a covered stent is used, it is possible to cure an aortic aneurysm, for example, and its clinical application has already begun. However, in the covered stent, the technique for bonding a metallic framework structural member with a covering material made of resin is not established yet: there are cases where the metallic framework structural member of a metallic stent makes a hole in a covering material made of polyester or polytetrafluoroethylene by piercing through it, or causes the covering material to wear away by rubbing, which results in decreases of its strength or its breakage.

For combining a metallic stent and a covering material made of resin, methods are contrived in which the covering material is fixed to the metallic stent by stitching the covering material with a thread or by wrapping the inner and outer surfaces of the metallic stent with the covering material. Since a film of PTFE porous material tends to tear easily when it is stitched with a thread, there are proposed methods in which the inner and outer surfaces of a metallic stent are simply covered with a covering material, or in which the covering material and the metallic stent are bonded together with a plastic resin or the like disposed therebetween as an adhesive. See Japanese Patent Application Publication No. H7-24072, Japanese translation of PCT international Application Publication No. 2000-508216, Japanese translation of PCT international Application No. 2002-510985, and Japanese translation of PCT international application No. 9-501584.

However, since the technique for uniting a covering material and framework structural member together by bonding the covering material along the surface of each element (e.g., metal wire part) of the framework structural member has not been developed yet, there has been a shortcoming that a sufficient strength and durability cannot be achieved because of a crack that occurs between the covering material and an element of the framework structural member.

More specifically, in the case where a covered stent 144 has a construction in which a framework structural member is covered with PTFE porous membranes 141 and 143 as shown in a sectional view of FIG. 14(A), it is impossible to bond the PTFE porous membranes in close contact along the surface of each element of the framework structural member 142, which results in generation of cracks (cavities), although it is possible to bond the PTFE porous membranes together by making them to contact with each other at intervallic gaps between the respective elements of the framework structural member 142 if the pitch of an interval between the respective elements of the framework structural member 142 is sufficiently large. As shown in a partial sectional view of FIG. 14(B), even if an adhesive 148 is used, the PTFE porous membranes 141 and 143 are partially in contact with each other, and also partially contact each element of the framework structural member 142, whereby only partial bonding is achieved (for example, contact adhesion parts 147 and 145), allowing occurrence of gaps 146.

Moreover, it is extremely difficult to make the PTFE porous membranes to adhere along the surface of each element of the framework structural member by fusion or bonding by means of heating since the tension of a planar direction is increased because the PTFE porous membranes shrink by heating. Particularly, when a net-like structure, which is made by knitting metal wires at a narrow pitch of 3 mm or less, is used as a framework structure, it was almost impossible to make the PTFE porous membranes to adhere so as to be fixed to the surface of each complicated and thin element of the framework structure.

More specifically, as shown in a sectional view of FIG. 15(A), in a covered stent 154 having a configuration in which a framework structural member is covered with PTFE porous membranes 151 and 153, it is also difficult to bond the PTFE porous membranes 151 and 153 together partially in contact with each other at intervallic gaps when the pitch of an interval between the respective elements of the framework structural member 152 is small, and it is only possible to partially bond the PTFE porous membranes with the respective elements of the framework structural member. As shown in a partial sectional view of FIG. 15(B), even if an adhesive 157 is used, the PTFE porous membranes 151 and 153 are partially in contact with each element of the framework structural member 152 so as to be bonded therewith (155), and it is impossible to prevent the occurrence of gaps 156.

A conceivable method for preventing the occurrence of such a crack (cavity) is to fill a resinous adhesive fully in a space 164 between PTFE porous membranes 161 and 163 and a framework structural member 162 so as to unite them as shown in a partial sectional view of FIG. 16. Also, in the case of FIG. 17, it might be considered to fill a gap 174 with an adhesive when the pitch of the intervallic gap between the respective elements of a framework structural member 172 is small. However, since the adhesive buried in the gap between PTFE porous membranes 171 and 173 restricts the transformation of the framework structural member 172, the flexibility and the elasticity of the covered stent would be degraded. The covered stent without flexibility and expandable/shrinkable property will be unusable as a stent-graft that is required to exhibit a property of expanding/shrinking in a radial direction.

Japanese Patent Application Publication No. H7-24072 proposes a method in which a covered stent is manufactured by providing covering layers made of a PTFE porous membrane on both the inner and outer superficies of a tubular structure composed of elastic wires such as metal wires, and partially bonding the so-provided inner and outer PTFE porous membrane covering-layers together by hot-melt adhesion. However, the examples of this method include only a point adhesion or a line adhesion made at some parts of the PTFE porous membrane covering layers: there are no bonding made between a metallic stent and the respective PTFE porous membrane.

In the above-mentioned method, it might be conceivable that the PTFE porous membranes can be completely bonded together by hot-melt adhesion using a heat press machine and a mold with which the inner and outer PTFE porous membranes can be heated while a pressure is applied to the PTFE porous membranes. In this method, however, it is preferable to minimize an oppressive force applied from a lopsided local direction since the porous structure of the PTFE porous membrane tends to break from the part which is crushed by the oppressive force thus applied. Therefore, it is preferable to apply homogeneous pressure in the normal direction of the surface of the covered stent which is formed providing covering layers made of PTFE porous membranes on the inner and outer sides of the tubular structure composed of elastic wires. However, it is substantially only in one direction that a mold can apply homogeneous pressure to most part of the covered stent surface.

As concretely shown in a sectional view of FIG. 18, a covered stent, which is formed by providing covering layers made of PTFE porous membranes 182 and 184 over the inner and outer surfaces of a tubular structure 183 composed of elastic wires, is placed on the circumferential surface of a mandrel 181, and split dies 185-192 are arranged on the outside of the outer covering layer. Under such conditions, the inner and outer PTFE porous membranes are bonded together as a result of hot-melt adhesion caused by applying pressure and heat onto these split dies. In this method, the direction of the pressure of each split die is applied substantially in one axial direction. Moreover, the elastic wires, which are the constituting elements of the tubular structure 183, protrude, and therefore it is necessary to provide rather loose trenches 193 at the corresponding parts of the mold in order to prevent the porous structure of the PTFE porous membranes from being crushed or torn by pressure centering on the protruded parts (FIG. 19). However, in the case of the covered stent, it is substantially impossible to prepare a mold suitable for such a framework structural member or to adjust the positioning of the mold and the covered stent because in many cases the framework structural member has a shape formed by minutely complicated knitting. Moreover, as shown in a sectional view of FIG. 19, it is impossible to prevent the occurrence of crack (cavity) 194 even if an adhesive 195 is used in this method.

Because of the above-mentioned problems, the products for which a mold can be used is limited to those of smooth planar shape (plain film-like shape) or nearly equivalent to such a shape. Therefore, with a mold it is extremely difficult or substantially impossible to manufacture a covered stent having a cylindrical shape, tapered shape, bifurcated configuration, bow configuration, or a combination of these forms. Particularly, with a mold, it is practically impossible to manufacture a covered stent of custom-made form adjusted to the figure of a patient or the shape and size of a lesion part: much less those of 3-D asymmetry shape.

In order to firmly unite a framework structural member and a PTFE porous membrane together, it is preferable that a fluoroplastics layer such as an unsintered PTFE layer be interposed therebetween as an adhesive and the adhesive be fused by heating while pressure is applied so that they may be bonded together. However, in this method, since a mold for hot press must be heated to a high temperature of about 250° C. to 380° C., the applied heat tends to warp a mold, or cause the surface to oxidize, thereby making the mold fragile. Therefore, it is difficult to maintain the precision and the durability of the mold in the manufacture of industrial scale. Particularly, with a mold, it is extremely difficult to form thin PTFE porous membranes of 0.1 mm or less into a multiple layer.

Moreover, in the manufacture of a covered stent, the mold-releasing agent cannot be used for preventing residues from remaining in a product, and the consequent shortcoming is that the product tends to adhere to the mold heated at high temperature, thereby causing the product to tear at the time of removal from the mold. Such a problem is particularly great in the case of a product having a framework structural member of finely complicated shape in which the unevenness easily occurs.

DISCLOSURE OF THE INVENTION

An object of the present invention is to provide a composite structure and a manufacturing method thereof, wherein the composite structure is formed by sandwiching a framework structural member between two porous PTFE layers, the framework structural member having a plurality of gaps or openings, and wherein substantially complete bonding is achieved not only between the porous PTFE layers, but also between the respective porous PTFE layers and the respective elements of the framework structural member, whereby they are unified.

Another object of the present invention is to provide a composite structure and a manufacturing method thereof, wherein the composite structure having an unified configuration as described above and having superior characteristics such as flexibility, expandable/shrinkable property, mechanical strength, durability, etc., is suitable for use as a covered stent or the like.

As a result of having intensively studied in order to achieve the objects, the present inventors conceived of a method in which an intermediate composite material is made by sandwiching a framework structural member between two porous PTFE layers, laying the intermediate composite material in a mass of fine particles, and applying pressure at least from one outside of the porous PTFE layers through the mass of fine particles on which the pressure is applied from the outside.

When the method of the present invention for applying pressure through a mass of fine particles is adopted, the pressure can be applied on the whole surface of a porous PTFE layer substantially equally, whereby not only can porous PTFE layers be adhered together through the gaps or openings of a framework structural member, but also the respective porous PTFE layers and the respective elements of the framework structural member can be united closely along the surfaces of the respective elements in such a manner as to wrap the respective elements with the porous PTFE layers. According to the method of the present invention, since the pressure can be applied substantially equally, the porous PTFE layer will not tear partially nor will the porous structure be damaged.

Moreover, according to a method of the present invention, by heating a mass of fine particles, it is possible to achieve hot-melt adhesion of the respective contact parts or the hot-melt adhesion thereof through fluoroplastics. Therefore, the mass of fine particles should preferably be composed of materials, such as inorganic particles, that will not suffer from transformation in their shapes when heated at a temperature lower than the pyrolysis temperature of PTFE. When an unsintered porous PTFE layer is used, it is possible to sinter at the time of heating. According to the method of the present invention, the above-mentioned problems due to the use of a mold do not occur, because no mold is used. With the method of the present invention, since the adherence of substantially whole parts of the composite structure can be achieved, the adhesive layer becomes an extremely thin even when a fluoroplastics layer is interposed as an adhesive, and therefore the flexibility and deformability (expandable/shrinkable property) of the composite structure will not be damaged.

According to the present invention, even if a framework structural member having a complicated and fine configuration is used, it is possible to manufacture a composite structure such as a covered stent having a cylindrical shape, tapered shape, bifurcated configuration, bow configuration, or combination of these shapes. Moreover, it is possible to manufacture a composite structure of 3-D asymmetry shape and a covered stent having a custom-made form adjusted to fit the figure of a patient, the shape and size of a lesion part, etc. The composite structure of the present invention is superior in the flexibility, mechanical strength, durability, etc.

By controlling the conditions of application of pressure and heating, the method of the present invention can generally be applied to a method of laminating macromolecular materials. The present invention is completed based on such knowledge.

Thus, a composite structure provided according to one embodiment of the present invention comprises a polytetrafluoroethylene porous layer (A1), a polytetrafluoroethylene porous layer (A2), and a framework structural member having a plurality of gaps or openings, the framework structural member being disposed between the polytetrafluoroethylene porous layers (A1) and (A2), and the composite structure is characterized in that:
  (1) the polytetrafluoroethylene porous layers (A1) and (A2) are united together by being adhered with each other through the gaps or openings of the framework structural member; and
  (2) the respective polytetrafluoroethylene porous layers (A1) and (A2) are united with the framework structural member closely along the surfaces of the respective constituent elements of the framework structural member in such a manner as to wrap the respective elements.

According to one aspect of the present invention, a method of manufacturing a composite structure comprising a polytetrafluoroethylene porous layer (A1), a polytetrafluoroethylene porous layer (A2), and a framework structural member having a plurality of gaps or openings is provided, the method being characterized in that the method includes the following Steps 1 through 3:
  (A) Step 1 for preparing an intermediate composite material which is formed by sandwiching a framework structural member between the polytetrafluoroethylene porous material layers (A1) and (A2);
  (B) Step 2 for applying pressure at least from one outside of the polytetrafluoroethylene porous layers (A1) and (A2) through a mass of fine particles so that the polytetrafluoroethylene porous layers (A1) and (A2) can be adhered not only with each other through the gaps or openings of the framework structural member, but also with the framework structural member closely along the surfaces of the respective elements of the framework structural member in such a manner as to wrap the respective elements; and
  (C) Step 3 for uniting the respective adhered parts by heating at a temperature lower than the pyrolysis temperature of polytetrafluoroethylene in a state where pressure is applied.

Another aspect of the present invention is to provide a method of manufacturing a tubular composite structure, the manufacturing method being characterized in that a tape-like composite structure is spirally lapped around the circumferential surface of a cylindrical support block and the overlapping parts of the tape-like composite structure are bonded, wherein the tape-like composite structure is formed by arranging, between a polytetrafluoroethylene porous layer (A1) and a polytetrafluoroethylene porous layer (A2), a framework structural member that has a plurality of gaps or openings, and wherein the polytetrafluoroethylene porous layers (A1) and (A2) are united together in close contact not only with each other through the gaps or openings of the framework structural member, but also with the framework structural member along the surfaces of the respective elements of the framework structural member in such a manner as to wrap the respective elements.

According to yet another aspect of the present invention, a method of manufacturing a composite structure is provided, wherein the method includes a step of applying pressure from at least one outside surface of two layers of macromolecular material through a mass of fine particles, the two layers of macromolecular material having been stacked up directly or in a state in which a framework structural member having a plurality of openings or gaps is sandwiched therebetween.

According to the invention, a composite structure is provided wherein a framework structural member having a plurality of gaps or openings is arranged between two porous PTFE layers and wherein substantially whole contact is achieved not only between the porous PTFE layers but also between the respective porous PTFE layers and the respective elements of the framework structural member such that they are united together. The composite structure of the invention is superior in the flexibility, expandable/shrinkable property, mechanical strength, durability, etc. and is suitable for use as a covered stent or the like. Moreover, the method of the invention can generally be applied to a method of laminating macromolecular materials.

BEST MODE FOR CARRYING OUT THE INVENTION

Figure 1:
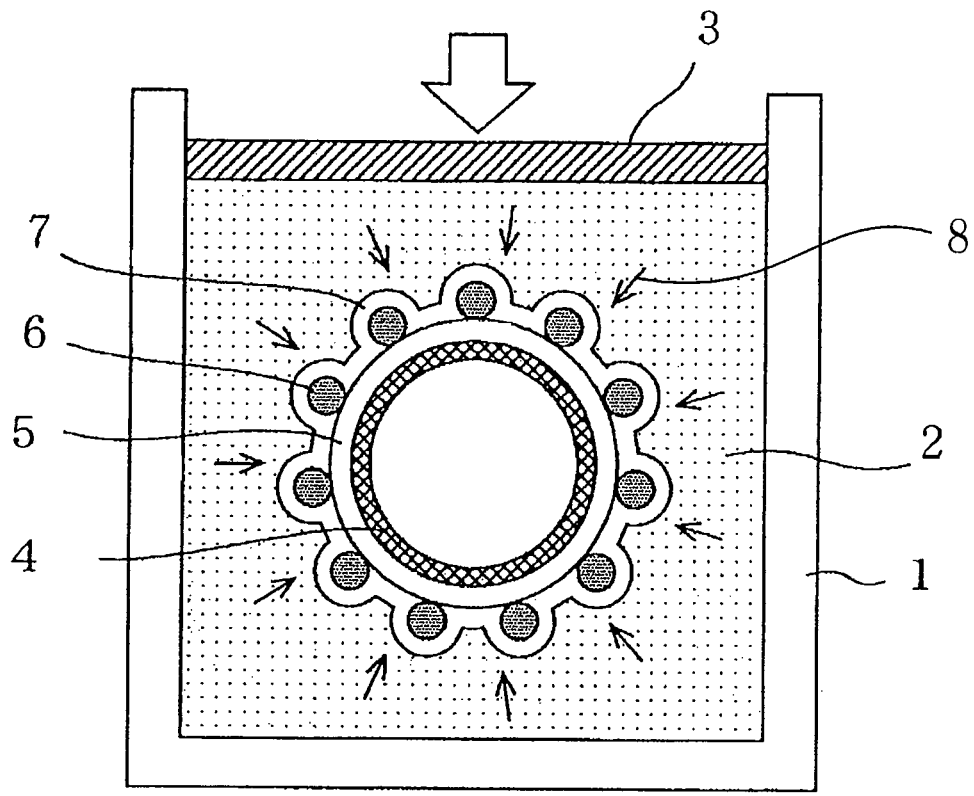
FIG. 1 is a sectional view showing an embodiment of a manufacturing method according to the present invention.

The PTFE porous material used in the present invention can be manufactured by the method described in Japanese Patent Application Examined Publication No. S42-13560, for example. First, an unsintered PTFE powder mixed with a liquid lubricant is formed by RAM press into a tubular, rod-like, or board-like shape. If it is necessary to obtain a sheet form having a thin thickness, a plate-shaped unsintered PTFE is subjected to rolling by a reduction roll. After the extrusion or rolling process, the liquid lubricant is removed from the extruded or rolled product if required. An unsintered PTFE porous material having a thin film-like form can be obtained by expanding the extruded or rolled product at least in one axial direction. A PTFE porous material having high strength can be produced by heating an unsintered PTFE porous material at a temperature not lower than 327° C., which is the melting point of PTFE, while it is fixed in order to prevent the contraction thereof, thereby sintering and solidification of the so-expanded configuration being accomplished.

An unsintered PTFE porous material is called an unsintered article and the heat of fusion thereof is 30 J/g or more. If such unsintered PTFE porous materials are used, the adhesive force between the PTFE porous materials as well as between the PTFE porous material and the respective elements of the framework structural member can be enhanced. On the other hand, since the strength of the unsintered PTFE porous material is weak and the handling thereof is difficult, a sintered PTFE porous material in which the strength is increased by sintering may be used. The heat of fusion of the sintered PTFE porous material is less than 30 J/g. A PTFE porous material is used generally in a form of a tube or a sheet (including a tape, a ribbon, or the like). The PTFE porous material is called "porous PTFE layer" in the present invention, since it is generally of membrane-like shape with thin thickness.

The porosity and the pore size of the PTFE porous material can be set to the desired value by adjusting the expansion ratio and the expansion conditions. When a composite structure of the present invention is applied to such a use as a stent-graft, a blood vessel prosthetic device, or the like, the PTFE porous material to be used has, preferably, a film thickness of 100 μm or less and a porosity of 40% or more, and more preferably, a film thickness of 80 μm or less and a porosity of 60% or more, so that flexibility and the decrease of outer diameter in the case of being folded can be achieved. In many cases, it is desirable to make the film thickness of the PTFE porous material equal to or less than 50 μm, and more preferably, equal to or less than 30 μm. From the viewpoint of strength, the minimum film thickness is 10 μm in general, and about 15 μm in many cases.

It is desirable to choose the pore size of a PTFE porous material in consideration of the position for which an article or device of the present invention is used. When a composite structure of the present invention is used as a stent for the cure of an aortic aneurysm of a large blood vessel having a caliber equal to or more than 10 mm, or the like, preferably the PTFE porous material has a bubble point of 500 kPa or less in the case of isopropyl alcohol, a pore size of 0.05 μm or more, and a fibril length of 1 μm (average fibril length) or more. In the case where the composite structure of the present invention is used as a stent for the cure of arteriosclerosis obliterans, or the like, of peripheral arteries having a caliber of 6 mm or less, it is preferable that the PTFE porous material have a bubble point of 50 kPa or less, a pore size of 0.2 µm or more, and a fibril length of 20 µm or more. From the viewpoint of the recovery nature, the PTFE porous material may have a bubble point of 1 kPa or less, a pore size of 0.5 µm or more, and a fibril length of 60 µm or more. The pore size of the PTFE porous material is preferably about 0.2-1 µm, but from the viewpoint of the recovery nature, may be 5 µm or more.

The "framework structural member having a plurality of gaps or openings" as used in the present invention are, for example, a network and a mesh which are made by knitting elastic wires such as metal wires, a tubular structure composed of elastic wires, a wire braid (tube made by knitting thin metal wires), a spiral zigzag wire structure, a net-like structure (for example, a metallic film in which a net-like structure is formed by cutting away parts thereof with a laser), an expandable metal, etc. The networks, meshes, and tubular structures which are composed of elastic wires such as metal wires, etc. have many gaps for reticulations. Likewise, the net-like structure formed by cutting out parts of a metallic film with the laser, the expandable metal, etc. have many openings. These gaps and openings are through-holes.

A network, mesh, tubular structure, or the like which is made beforehand can be used as a framework structural member. However, in a process of preparing a composite structure, the framework structural member may be formed by arranging a plurality of elastic wires such as metal wires with intervals therebetween, or arranging one or more zigzag shaped elastic wires, on a porous PTFE layer (A1), and by covering another porous PTFE layer (A2) thereon, for example.

The shape of the framework structural member, and the number and size of the gaps and openings thereof, etc. can be chosen depending on the purpose of its use. A metal wire is generally used as the elastic wire, although a monofilament or fiber made of heat resistant resin may be used. The framework structural member may be made of a material, such as stainless steel, nickel alloy, titanium, titanium alloy, etc. In the case where the composite structure of the present invention is used for a medical use, such as a stent, the particularly suitable materials of the framework structural member are, for example, a transplantable stainless steel, nickel alloy, and titanium alloy for the medical treatment. The diameter of the elastic wire such as a metal wire is preferably about 0.05-1 mm, and more preferably about 0.1-0.5 mm; depending on the use, the diameter may be larger.

In the case where the framework structural member is a tubular structure, it is desirable that the tubular structure be radially expandable/shrinkable. More specifically, preferably the tubular structure is structured such that the elastic wire such as a metal wire is bendable, and connectable according to need, and such that not only can the tubular structure be elastically compressed so as to be inserted in a passage having a caliber smaller than the original size, but also it can be recovered to the original shape when the elastic restoration force is released. Such a tubular structure is disclosed, for example, in Japanese Patent Application Publication No. H7-24072, etc. The framework structural member having such features may be a tubular structure made beforehand using elastic wires; however, it may be formed in a process of forming a composite structure.

The element constituting a framework structural member is an elastic wire (including a part) in the case where the framework structural member is formed using the elastic wires. In the case where the framework structural member is a metallic film in which many openings are formed by using the laser, or is an expandable metal having many openings therein, or the like, the part excluding the openings is a constituent element.

The composite structure of the present invention has a configuration in which a framework structural member having a plurality of gaps or openings is arranged between a porous PTFE layer (A1) and a porous PTFE layer (A2). Such composite structure is manufactured in the following manner. First, in Step 1, an intermediate composite material is prepared in which a framework structural member is inserted between the porous PTFE layers (A1) and (A2). The respective porous PTFE layer may be a separate tube or sheet. Or otherwise, a framework structural member may be sandwiched therebetween by turning back a tubular PTFE porous material, or by folding one sheet of PTFE porous material.

Next, in Step 2, pressure is applied through a mass of fine particles on the intermediate composite material prepared in Step 1. More specifically, the pressure is applied on the intermediate composite material through the mass of fine particles from the outer surface of at least one of the porous PTFE layers (A1) and (A2). Consequently, the porous PTFE layers (A1) and (A2) are adhered each other through the gaps or openings of the framework structural member, and moreover they are respectively adhered with the respective constituent elements of the framework structural member closely along the surfaces of the respective elements in such a manner as to wrap them.

In Step 2, in the case where the shape of the intermediate composite material is tubular, the intermediate composite material, which is formed by arranging the porous PTFE layer (A1), the framework structural member, and the porous PTFE layer (A2) in the enumerated order, is placed on around the circumferential surface of a cylindrical support block (e.g., mandrel, mold). In this state, pressure is applied through a mass of fine particles from the outer surface of the porous PTFE layer (A2). In the case of an intermediate composite material having a sheet-like shape, pressure may be applied from the outer surfaces of both the porous PTFE layers (A1) and (A2); or the sheet-like intermediate composite material may be placed on a planar support block with the porous PTFE layer (A1) side being disposed thereon, and in this condition, pressure may be applied from the outer surface of the porous PTFE layer (A2). After Step 2, in Step 3, the respective adhered parts are integrated by heating the intermediate composite material at a temperature lower than the pyrolysis temperature of PTFE while pressure is applied.

In order to unite two porous PTFE layers in a manner such that a framework structural member is sandwiched between porous PTFE layers, and such that the porous PTFE layers are adhered to the respective elements of the framework structural member so as to wrap them along the surface thereof, it is essential to heat at high temperature and to apply substantially equal pressure from the outer surface of at least one of the porous PTFE layers. However, it is impossible to unite the porous PTFE layer and a framework structural member together in such a manner as to make them to contact in their entire surfaces, because when heated at high temperature, the porous PTFE layer prepared by expansion tends to shrink in the direction opposite to the direction in which the previous expansion was performed, and accordingly the porous PTFE layers are caused to loosely drift without adhering to the respective elements of the framework structural member. Such tendency increases as the heating temperature becomes higher, the thickness of the element of the framework structural member becomes larger, and the shape of the framework structural member becomes more complicated.

On the other hand, according to the method of the present invention in which pressure is applied through a mass of fine particles, the above-mentioned problem can be overcome. Hereinafter, the method of the present invention will be explained referring to FIGS. 1 and 2. FIG. 1 is a sectional view which shows an application example of the method of the present invention. An intermediate composite material, which is formed by arranging a porous PTFE layer 5, a framework structural member 6, and a porous PTFE layer 7 in the enumerated order, is placed on around the circumferential surface of a mandrel (mold) 4. In the state in which the intermediate composite material is placed on the surface of the cylindrical support block, the intermediate composite material is put in a container 1. Fine particles are put in the container 1 beforehand, and after putting the intermediate composite material in the container, fine particles are added thereon. Thus, the intermediate composite material is placed in the mass of fine particles 2. Here, the container used as the container 1 is preferably a pressure-resistant heat-resistant container made of stainless steel, for example.

A board 3 is put on the top surface of the mass of fine particles 2, and pressure is applied to the mass of fine particles by the self-weight of the board 3 and pressure applied from the outside. The board 3 is preferably a stainless steel board having a pressure-resistant and heat resistant properties, for example. The pressure from the outside can be applied by putting a weight on the board 3 or applying mechanical pressure. When the pressure is applied from the outside in this manner, substantially equal pressure 8 is applied on the entire outer surface of the intermediate composite material from the outer surface of the porous PTFE layer 7 of the intermediate composite material through the mass of fine particles due to the inherent characteristics of the mass of fine particles. Preferably, the pressure afforded by the mass of fine particles is made uniform as much as possible, for example, by vibration caused by beating the container 1 with a hammer, in addition to applying the pressure. The degree of the pressure to be applied can be determined appropriately according to the shape of the framework structural member, the thickness of the porous PTFE layer, etc.; however, preferably, the pressure is 1 kPa or higher, and more preferably, 3 kPa or higher.

By adopting the method of applying pressure through the mass of fine particles, substantially equal pressure is applied to the entire surface of the PTFE porous material 7. As a result, the porous PTFE layer 7 adheres to the respective elements of the framework structural member 6 along the surface of the respective elements in a manner such that the respective elements are wrapped therein, without the porous structure of the porous PTFE layer being broken or the porous PTFE layer being torn. When the whole of the container 1 is heated at high temperature in the state where the pressure is applied in this manner, the respective adhered parts are integrated by the fusion-bonding.

The method of heating the whole of a container is, for example, such that the container is heated for a predetermined time by being put in a hot-blast circulated thermostatic vessel which is heated at a given temperature. The heating temperature is adjusted to a temperature lower than 380° C. which is the pyrolysis temperature of PTFE. If the lowest heating temperature is sufficiently high for uniting the respective adhered parts under the condition where pressure is applied, it may be a temperature (e.g. about 255° C.) lower than 327° C. which is the melting point of PTFE. In the case where a framework structural member is wrapped with fluoroplastics as described later, the heating temperature is preferably a temperature equal to or higher than the melting point of the fluoroplastics. In many cases, it is preferable to set the heating temperature to a temperature equal to or higher than 327° C., which is the melting point of PTFE, so that the respective contact parts can be united stably by fusion bonding. The heating time is generally about 10 minutes to 10 hours, and preferably about 30 minutes-5 hours, depending on the heating temperature.

Figure 2:
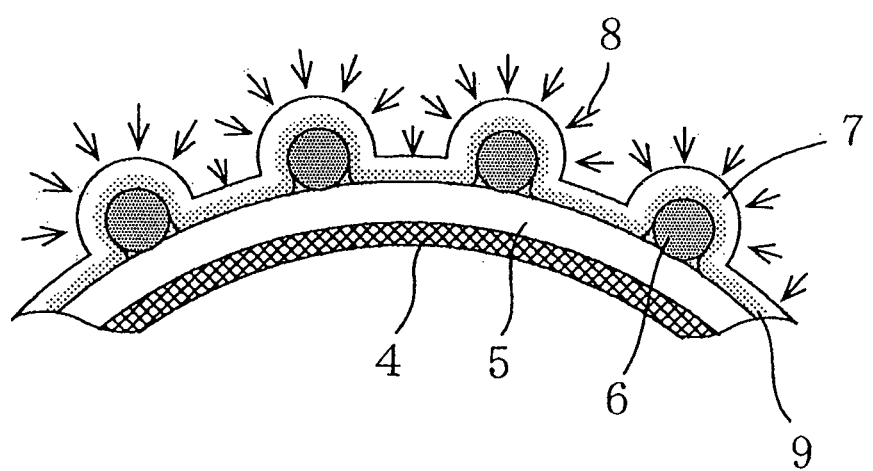
FIG. 2 is a sectional view showing a manufacturing method according to an embodiment of the present invention, in which porous PTFE layers are in close contact along the surfaces of the respective elements (metal wires) of a framework structural member in a manner such that the respective elements are wrapped with them.

The above-described method makes it possible to form a composite structure in which the porous PTFE layers 5 and 7 are united together in close contact through the gaps or openings of the framework structural member, as shown in FIGS. 1 and 2, and moreover, the porous PTFE layers 5 and 7 are integrated with the framework structural member 6 in such a manner as to wrap the respective constituent elements of the framework structural member 6 in close contact along the surfaces of the respective elements. In this case, an adhesive layer 9 may be interposed.

Figure 14:
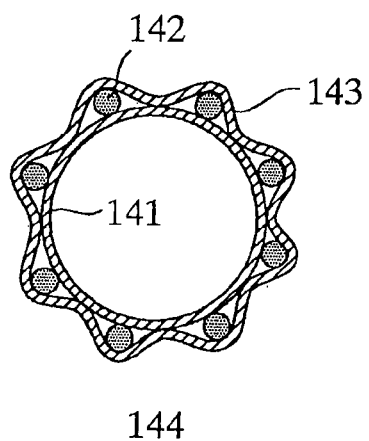
FIG. 14(A) and FIG. 14(B) are an explanatory views showing a laminating condition of a conventional composite structure.
Figure 14B:
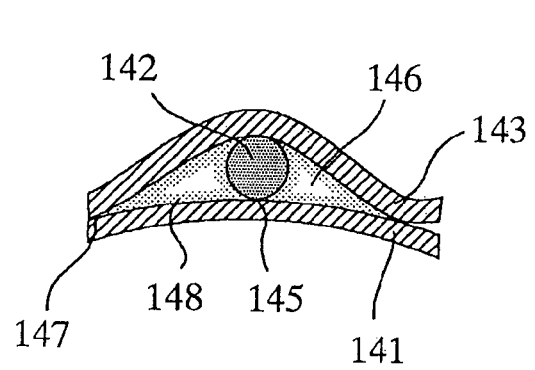
Figure 15:
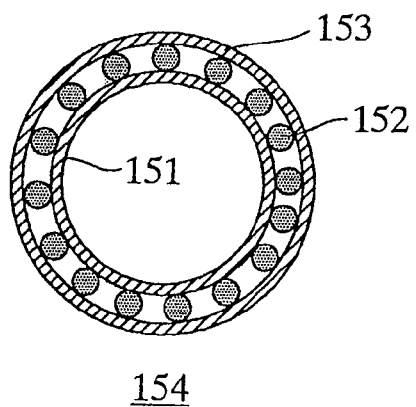
FIG. 15(A) and FIG. 15(B) are an explanatory views showing another laminating condition of a conventional composite structure.
Figure 15:
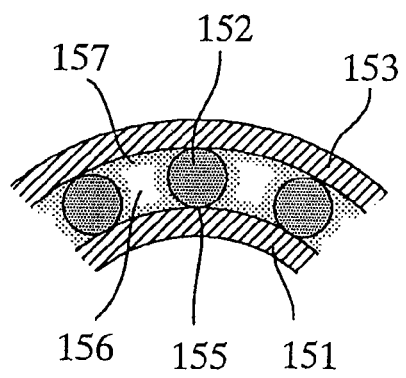

In the conventional method, large cracks 146 and 156 are caused as shown in FIGS. 14 and 15. In contrast, according to the method of the present invention, it is possible to make a composite structure including substantially no cracks (cavities) such that porous PTFE layers not only adhere with each other, but also adhere to the respective elements of the framework structural member in such a manner as to wrap them along the surfaces thereof as shown in FIGS. 1 and 2. Such close adherence of the porous PTFE layers may be achieved by their mutual cooperation along the surfaces of the respective elements of the framework structural member. Also, it does not matter if very small parts of the surface of the respective elements are not covered with the respective porous PTFE layer; it is sufficient if substantially no cracks exist.

The fine particles are not particularly limited in terms of kind if they can endure the pressure and heat treatment applied according to the method of the present invention; however, those which do not change in their form under the heat treatment at a temperature lower than the pyrolysis temperature of PTFE are preferable. In the case where a framework structural member is wrapped in with an interposed fluoroplastics layer as described later, the fine particles should preferably be those which do not change in their form at a temperature equal to or higher than the melting point of the fluoroplastics and lower than the pyrolysis temperature of PTFE, and most preferably, those which do not change in their form at a temperature equal to or higher than 327° C., which is the melting point of PTFE, and lower than the pyrolysis temperature of PTFE. More specifically, from the viewpoint of preparing a high quality composite structure, increasing workability in a manufacturing process, and improving the ease of handling, the desirable fine particles are those which do not melt or decompose, that is, those which do not change in the shape and characteristics, within the above-mentioned temperature range.

From the viewpoint of heat resistance, the fine particles are preferably inorganic particles, and the materials thereof are preferably inorganic materials such as aluminum oxide, calcium carbonate, silica, kaolin, clay, titanium oxide, zinc oxide, barium sulfate, or magnesium hydrate; soluble inorganic salt such as sodium chloride, or potassium chloride, for example. Of these materials, particles of aluminum oxide or calcium carbonate are particularly preferable. The soluble inorganic salt is preferable because it can be removed by washing after the manufacturing process.

The fine particle is preferably an amorphous or globular shape. The particle diameter of the fine particles can be determined depending on the shape of a product: at least 1 mm or less, preferably 0.5 mm or less in view of applying homogeneous pressure. The diameter of a fine particle is preferably 5-500 μm, and more preferably 10-300 μm. In the case where the material of fine particles is unsuitable for the removal by washing, a metallic foil or the like may be interposed between the mass of fine particles and the porous PTFE layer in order to avoid direct contact with the surface of the porous PTFE layer when the pressure is applied.

According to the method of the present invention, the framework structural member can be formed in a complicated shape, and accordingly, the composite structure can be made firmly united. In the case where the framework structural member is formed of a metal wire or a metallic film, it is preferable that the surface thereof is minutely roughened beforehand so that a firm consolidation can be accomplished. More specifically, the surface of the framework structural member may be subjected to surface roughening processing, such as sandblasting processing or processing by a sand paper, or the like.

In the method of the present invention, it is possible to interpose an adhesive between the porous PTFE layer and the framework structural member. Such adhesive is preferably a synthetic resin having heat resistant and adhesive properties, and more preferably fluoroplastics. The methods for enhancing the adhesiveness of the porous PTFE layer and the framework structural member include the following methods, for example: (1) a coating of fluoroplastics is applied on the surface of the framework structural member beforehand; (2) a fluoroplastics-dispersed solution is applied on the surface of the porous PTFE layer and dried beforehand; (3) a fluoroplastics film is placed between the framework structural member and the porous PTFE layer beforehand.

Of these methods, it is preferable to adopt the method in which a coating of fluoroplastics is applied on the surface of the framework structural member beforehand and the method in which a fluoroplastics-dispersed solution is applied on the surface of the porous PTFE layer and dried beforehand. Such methods of covering a fluoroplastics layer are suitable for manufacturing a tissue-invaded and cure facilitating-type stent-graft having a caliber of 6 mm or less. However, in some cases of the framework structural member having a configuration in which metal wires are braided so as to exhibit expandable/shrinkable properties, the use of an adhesive such as fluoroplastics hampers such expandable/shrinkable properties. In such case, it is preferable not to use the adhesive.

Figure 16:
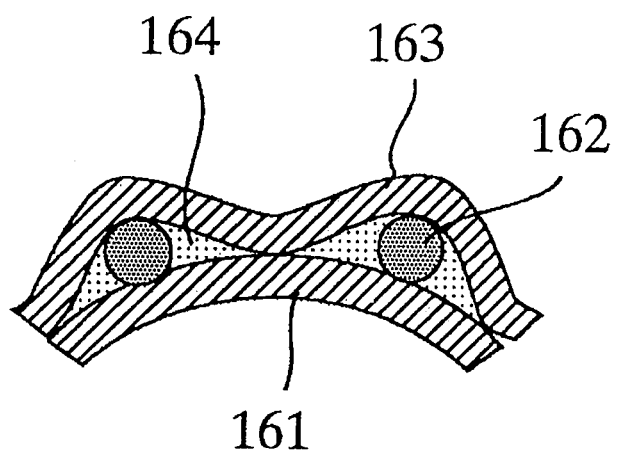
FIG. 16 is an explanatory view showing another laminating condition of a conventional composite structure.
Figure 17:
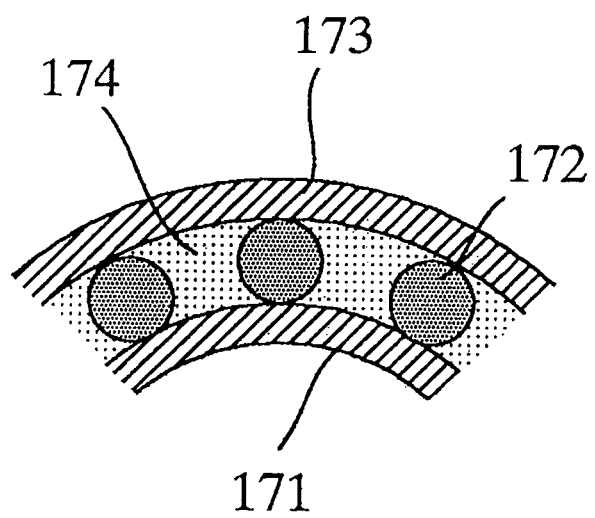
FIG. 17 is an explanatory view showing another laminating condition of a conventional composite structure.
Figure 18:
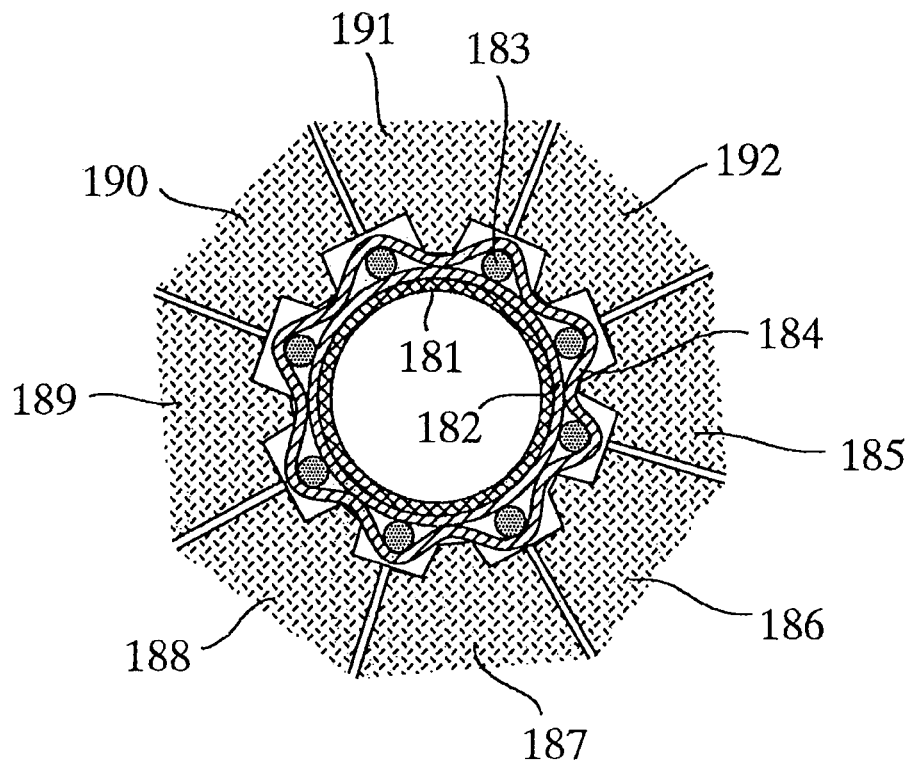
FIG. 18 is a sectional view showing an example of a method for manufacturing a composite structure using a mold.
Figure 19:
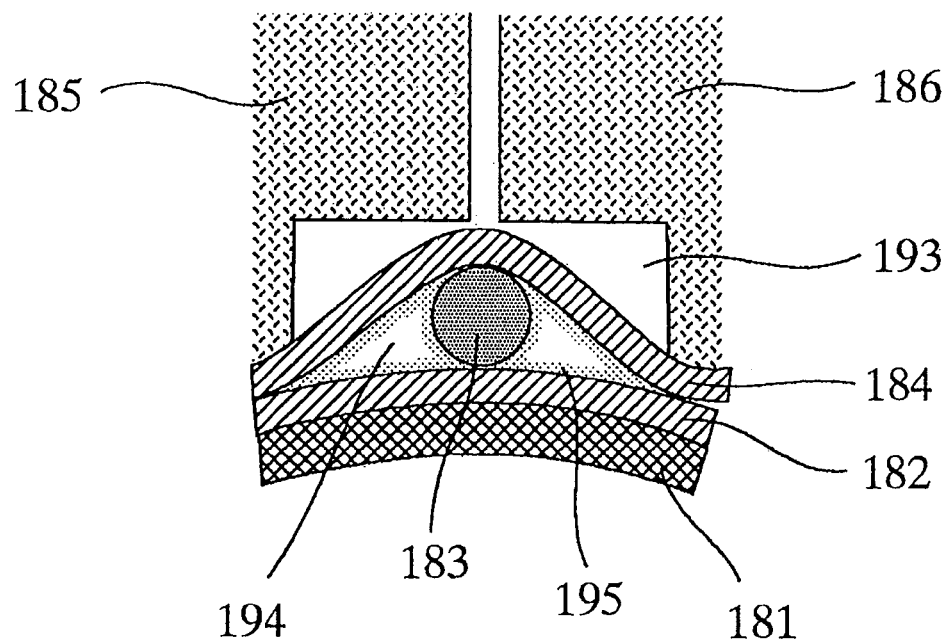
FIG. 19 is a sectional view showing an example of a method for manufacturing a composite structure using a mold.

When an adhesive such as fluoroplastics is heated at a temperature of the melting point thereof or higher while the pressure is applied, the adhesive melts and flows into the cracks between a porous PTFE layer and a framework structural member, so that a very firm integration thereof can be achieved by the fusion bonding with which the framework structural member and the porous PTFE layer are fixed. In the case where an adhesive is used in the conventional method, since the adhesive fills comparatively large cracks (cavities) 164 and 174 as shown in FIGS. 16 and 17, the flexibility and the expandable/shrinkable properties of the obtained composite structure are decreased. In contrast, according to the method of the present invention, since the porous PTFE layer is adhered to the respective elements of the framework structural member in such a manner as to wrap the respective elements along the surface thereof, the thickness of the adhesive layer made of fluoroplastics is very thin, and accordingly the flexibility and the expandable/shrinkable properties of the composite structure are hardly hampered. Moreover, with this adhesive, it is possible to form a nonporous intermediate layer.

When a tubular composite structure in which a nonporous intermediate layer is formed is used as a stent-graft for an aortic aneurysm cure, for example, the re-growth of the aortic aneurysm that may be caused due to the seeping out of serum permeating through the wall can be prevented.

Preferably, the resin as an adhesive has a melting point which is lower than 380° C., the pyrolysis temperature of PTFE, and has a pyrolysis temperature which is equal to or higher than the melting point of the porous PTFE. Also, for maintaining the characteristics of the porous PTFE layer, the resin as an adhesive is preferably fluoroplastics. Moreover, when the composite structure of the present invention is used for an end-vascular stent-graft, it is preferable to use PTFE, the tetrafluoroethylene/hexafluoropropylene copolymer (FEP), etc. which have established records for use as a main unit or reinforcement material for an artificial blood vessel, etc. The PTFE used as an adhesive is unsintered one. Other fluoroplastics such as FEP has heat-melting property.

Figure 3:
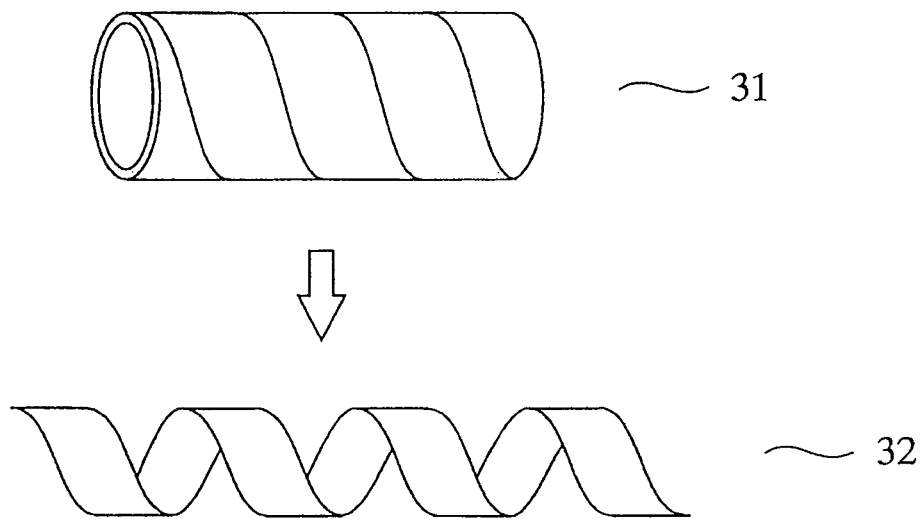
FIG. 3 is a schematic drawing showing an example of a mandrel used by a manufacturing method of the present invention.

It is preferable to use a mandrel (mold) as a cylindrical support block in order to implement the method of the present invention. Such mandrel is suitable for manufacturing a tubular stent-graft, for example. The mandrel for supporting a tubular composite structure is preferably structured such that the outer diameter be flexible enough to shrink in order to facilitate placing and removal of the composite structure. For example, FIG. 3 shows a mandrel 31 which is made by lapping a stainless steel plate spirally into a tubular form. The mandrel of such configuration can be made, by expanding or applying torsion, to exhibit a shape 32 in which the outer diameter is decreased.

Figure 4:
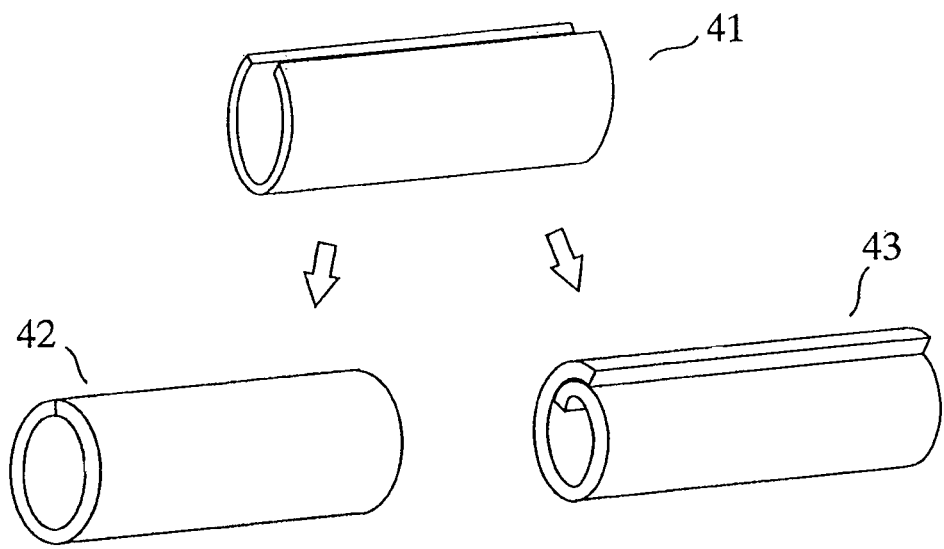
FIG. 4 is a schematic drawing showing another example of a mandrel used by a manufacturing method of the present invention.

FIG. 4 shows a mandrel 41 formed by merely winding a stainless steel board into a tubular form. It is possible to expand or to shrink the outer diameter of the mandrel 41 by inserting a rod thereinto or pulling out the rod therefrom, the rod having a diameter larger than the caliber of the mandrel 41. Also, since the mandrel 41 has a crack, a shape 42 having a reduced outer diameter can be formed if the crack is eliminated, and a shape 43 having a further reduced outer diameter can be formed if the end portions of the mandrel 41 are overlapped.

Figure 5:
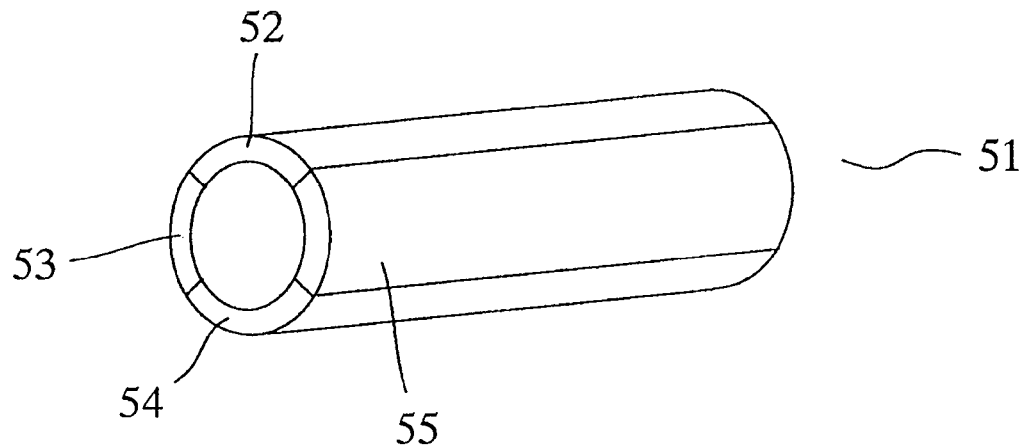
FIG. 5 is a schematic drawing showing another example of a mandrel used by a manufacturing method of the present invention.

FIG. 5 shows a hollow mandrel 51 which is made by combining boards each having a curved shape so that the desired shape and size of the mandrel can be obtained by combining the boards. By disassembling parts 52 through 55, the mandrel 51 can be separated from a tubular composite structure.

The material of the boards used for such mandrels is not particularly limited except that the characteristics thereof must not change under the heat treatment conditions and that they must have elasticity and stiffness of some degree: for example, a stainless steel board is preferable. The thickness of the board is preferably 5 mm or less, and more preferably 0.5 mm or less so that it may not affected by the thermal distortion. The allowable minimum thickness of the board is about 0.5 mm, and more preferably about 0.1 mm.

Figure 6:
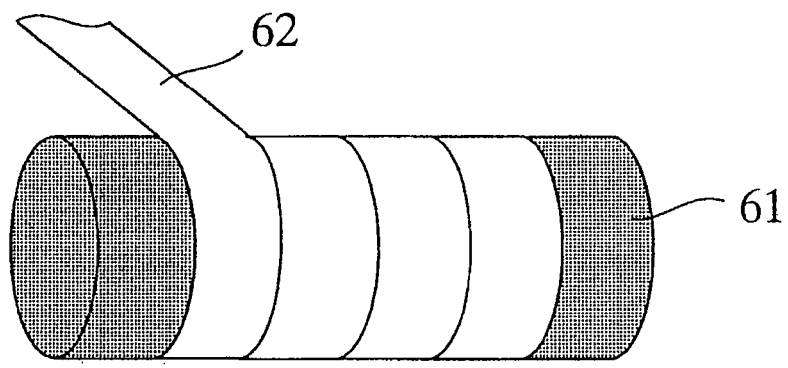
FIG. 6 is an explanatory view showing an embodiment of a manufacturing method according to the present invention.
Figure 7:
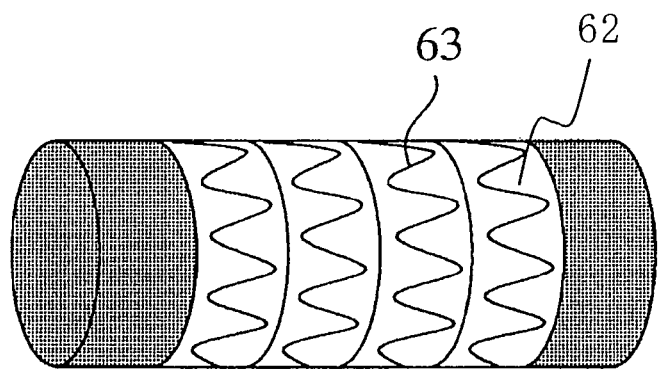
FIG. 7 is an explanatory view showing an embodiment of a manufacturing method according to the present invention.
Figure 8:
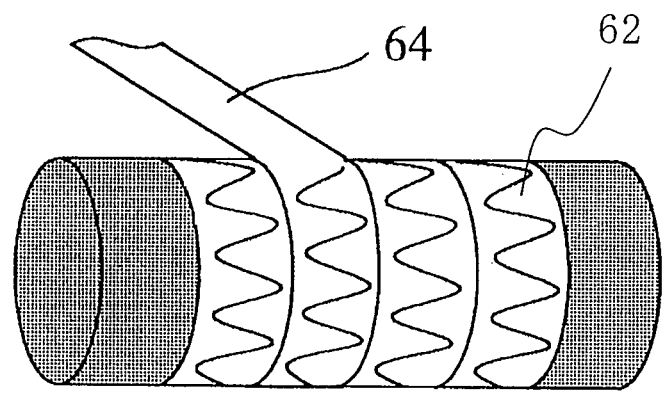
FIG. 8 is an explanatory view showing an embodiment of a manufacturing method according to the present invention.
Figure 9:
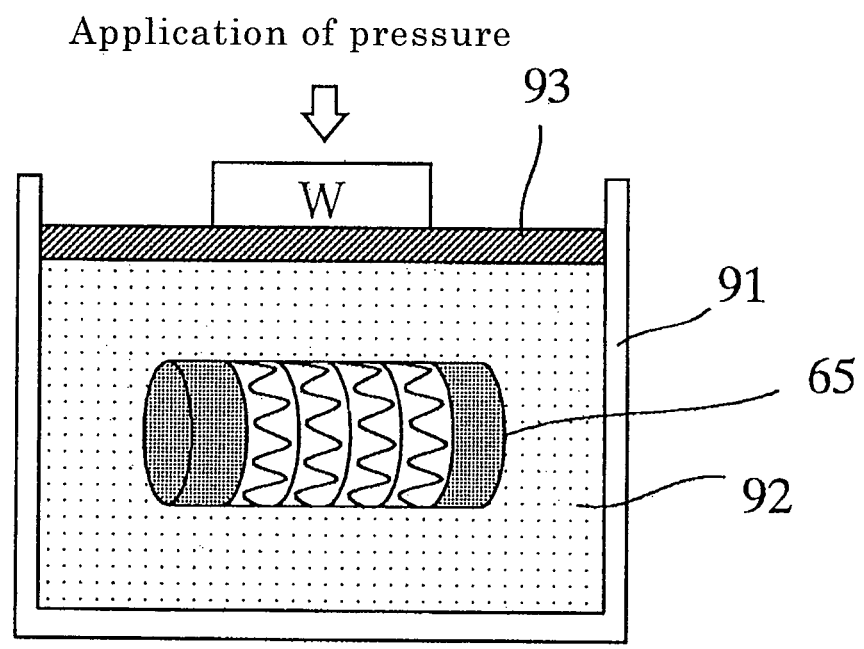
FIG. 9 is an explanatory view showing an embodiment of a manufacturing method according to the present invention.

An example of the methods of the present invention will be explained, referring to FIGS. 6 through 9. FIG. 6 shows a process of forming a first layer by winding a tape-like porous PTFE layer 62 spirally around the circumferential surface of a mandrel 61. FIG. 7 shows a process of arranging a zigzag-shaped elastic wire (e.g., metal wire) 63 on the porous PTFE layer 62. FIG. 8 shows a process of making a sandwich configuration by winding a porous PTFE layer 64 spirally over the elastic wire 63. FIG. 9 shows a process in which an intermediate composite material 65 having the sandwich configuration is, together with the mandrel, put in a container 91 containing fine particles, and then fine particles are added thereon such that the intermediate composite material is buried in a mass of fine particles 92. Thereafter, a board 93 is placed on the mass of fine particles 92, and pressure is applied on the intermediate composite material 65 through the mass of fine particles.

By affording vibration to the container 91 when pressure is applied, the pressure can be more homogeneously applied in all directions. In this case, according to the shape and size of the composite structure, the pressure is adjusted to: preferably 1 kPa or more, and more preferably 3 kPa or more. The upper limit of the pressure is preferably about 15 kPa, and more preferably, about 10 kPa. The value of the pressure is calculated from the application degree of the pressure.

During or after the above-mentioned process of applying pressure, the container which contains the intermediate composite material and the mass of fine particles is heated for a given time in a heating furnace (e.g., hot-blast circulated thermostatic vessel) which is heated at a predetermined temperature. By this heat treatment, the mutually adhered parts of the porous PTFE layers and the respective adhered parts of the porous PTFE layers and the elements of the framework structural member are united by the fusion bonding.

Figure 10:
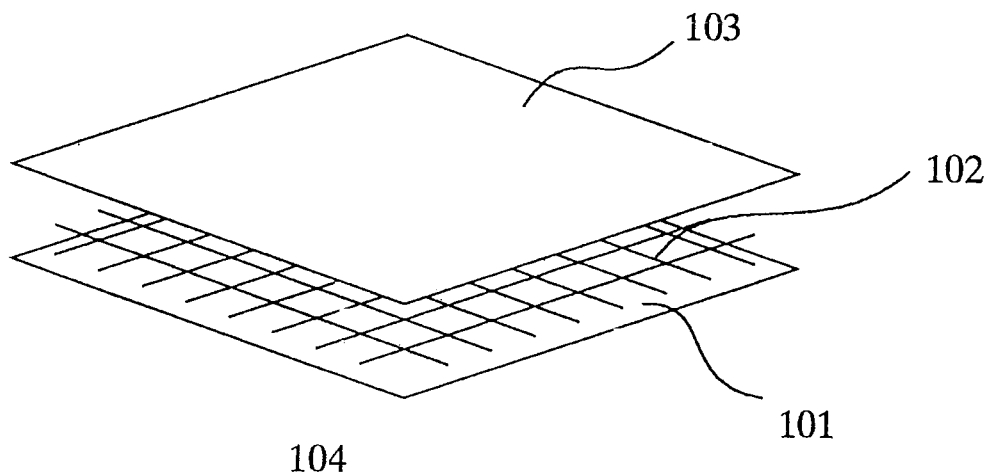
FIG. 10 is an explanatory view showing an example of a manufacturing process of a composite structure having a configuration in which both faces of a stainless steel wire net are covered with a porous PTFE layer.

FIG. 10 shows a process of manufacturing an intermediate composite material 104 in which a network 102 made by interweaving stainless steel wires in a lattice form are provided with porous PTFE layers 101 and 103 on both sides thereof. By laying the intermediate composite material 104 horizontally in the mass of fine particles and heating it while applying pressure, the intermediate composite material can be formed into a sheet-like composite structure.

Figure 11:
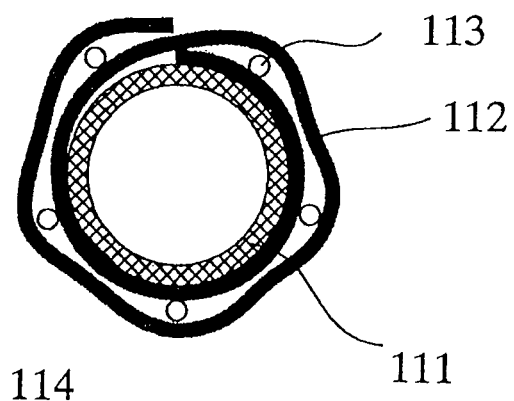
FIG. 11 is an explanatory view showing an example of a manufacturing process of a composite structure having a configuration in which stainless steel wires are covered with a porous PTFE layer.

FIG. 11 is a sectional view showing a process of manufacturing an intermediate composite material 114 in a manner such that a porous PTFE layer 112 is lapped around the circumferential surface of mandrel 111 into a two-laminated configuration wrapping a plurality of metal wires 113 therein. It is possible to form the intermediate composite material into a tubular composite structure by winding it around a mandrel and subjecting it to a heat treatment while applying pressure on it through a mass of fine particles in such state.

Figure 12:
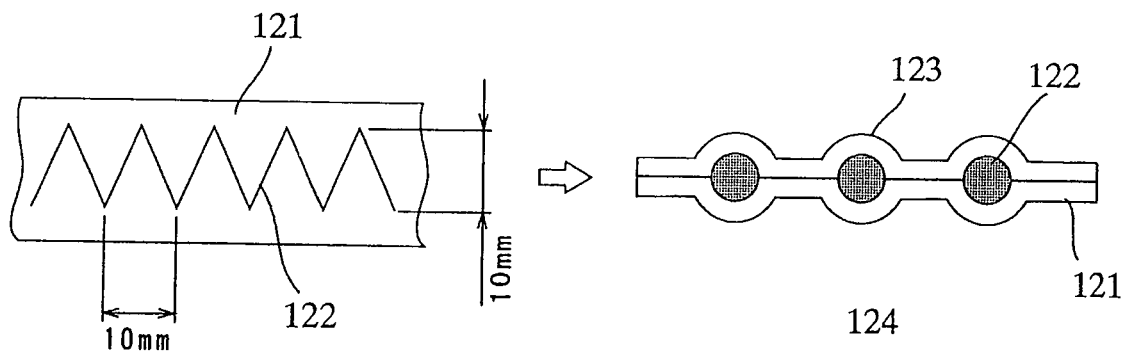
FIG. 12 is an explanatory view showing an example of a tape-like composite structure.
Figure 13:
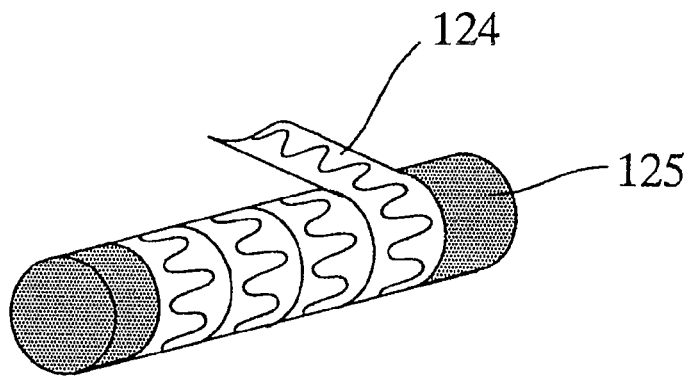
FIG. 13 is an explanatory view showing the process of preparing a tubular composite structure using a tape-like composite structure.

The composite structure of the present invention can be formed into a tubular composite structure by a secondary processing. By the method of the present invention, a composite structure 124 having a tape-like (also, ribbon-like) form is made such that an elastic wire 122 having a zigzag (crimp pattern) shape is arranged to be sandwiched between two porous PTFE layers 121 and 123 as shown in FIG. 12. Subsequently, the tape-like composite structure 124 can be processed into a tubular composite structure by winding it spirally around the circumferential surface of a mandrel 125 as shown in FIG. 13 and bonding the overlapped parts together. The bonding can be achieved using a hot-melt adhesion or an adhesive.

EXAMPLES

Hereinafter, Examples and Comparative Examples will be described in order to explain the present invention more specifically. However, the embodiments of the present invention is not limited to these Examples. The characteristics are measured by the measuring methods as follows.

The reinforcement drawing strength: a load that was needed to axially pull out a straight metal wire having a length of 20 mm that was embedded between two porous PTFE layers was measured as a reinforcement drawing strength. The method of preparation and measurement of samples: a metal wire was exposed leaving a part of 20 mm as it was sandwiched between the porous PTFE layers, and the metal wire was pulled out axially. The drawing rate was 20 mm/minute. The maximum load in this case was defined as a reinforcement drawing strength.

Example 1

A lattice-like network (a square form having a lateral length of 100 mm) in which a stainless steel wire having an outer diameter of 0.25 mm was braided at a pitch of 3 mm was placed between two unsintered PTFE porous membrane sheets [trade name: UP020-80 from Sumitomo Electric Industries, Ltd.] having a thickness of 80 μm, pore size of 0.2 μm, porosity of 80%, and square form of 100 mm in lateral length. (Refer to FIG. 10). The product thus prepared was put horizontally in a stainless steel container which contains a mass of calcium carbonate fine particles (the particle diameter: about 50 μm), and a mass of additional calcium carbonate fine particles were put in the container so as to cover the product placed therein.

Subsequently, a stainless steel board which was placed on the top of the mass of calcium carbonate fine particles was pressed from the upper side so as to apply a pressure of 6.2 kPa, and moreover the container was beaten with a plastic hammer so as to give vibration. This container was left for 2 hours in a hot-blast circulated thermostatic vessel which was set to a temperature of 340° C., and thereby a heat treatment was performed. Thereafter, as a result of rapid cooling with water, a unified structure of the stainless steel network and the PTFE porous membrane was obtained. The respective PTFE porous membrane layers were united by fusion bonding through narrow and thick knits (3 mm×3 mm; the maximum thickness: about 0.5 mm) of the stainless steel wires. It was confirmed that the PTFE porous membrane layers were integrated in close contact along the surfaces of the respective wires which were the constituent elements of the stainless steel wire network in a manner such that the wires were wrapped therewith.

Example 2

A mandrel having an outer diameter of 20 mm was prepared by spirally winding a stainless steel board having a thickness of 0.1 mm and a width of 15 mm into a tubular form. An unsintered PTFE porous membrane sheet having a width of 60 mm [trade name: UP020-80 from Sumitomo Electric Industries, Ltd.] was lapped around the circumferential surface of the mandrel so as to form a two layered configuration sandwiching five hard stainless steel wires each having a length of 60 mm (Japanese Industrial Standard SUS304, the outer diameter: 0.30 mm) as shown in FIG. 11. In this case, the hard stainless steel wires were arranged axially in parallel and with intervals at a pitch of about 10 mm.

The intermediate composite material thus prepared in a state of being wound around the mandrel was put horizontally into a stainless steel container which contains a mass of calcium carbonate fine particles (the particle diameter: about 50 μm), and a mass of additional calcium carbonate fine particles were put in the container so as to cover the intermediate composite material placed therein. Subsequently, a stainless steel board which was placed as a weight on the top of the mass of calcium carbonate fine particles was pressed from the upper side so as to apply a pressure of 3.1 kPa, and moreover the container was beaten with a plastic hammer so as to give vibration. Thereafter, the container was left for two hours in a hot-blast circulated thermostatic vessel which was set to a temperature of 340° C., and a heat treatment was performed. Thereafter, a rapid cooling was performed with water. Then, the mandrel was removed, and consequently a unified structure of the stainless steel network and the PTFE porous membrane was obtained.

In the tubular composite structure thus obtained, the respective PTFE porous membrane layers were united by fusion bonding through the gaps between the stainless steel wires. It was confirmed that the PTFE porous membrane layers were integrated in close contact along the surfaces of the respective wires in a manner such that the wires were wrapped therewith. The reinforcement drawing strength of the composite structure was 8±5 gf.

Example 3

A process in which a hard stainless steel wire having a length of 60 mm (the outer diameter: 0.30 mm) was immersed in a PTFE dispersion produced by Daikin Industries, LTD. (D1F) for about 5 to 10 seconds and subsequently dried at the normal temperature was repeated two or three times. Then, PTFE was applied onto the surface of the stainless steel wire. A unified structure of the stainless steel wire and the PTFE porous membrane was prepared in the same manner as in Example 2 except for the above-described process.

In the tubular composite structure thus obtained, the respective PTFE porous membrane layers were united by fusion bonding through the gaps between the stainless steel wires. In addition, it was confirmed that the PTFE porous membrane layers were integrated in close contact along the surfaces of the respective stainless steel wires in a manner such that the wires were wrapped therewith. The reinforcement drawing strength of the composite structure was improved to 293±72 gf.

Example 4

The surface of a hard stainless steel wire having a length of 60 mm (the outer diameter: 0.30 mm) was roughened by rubbing with a paper file of No. 1500. Then, the stainless steel wire was immersed in a PTFE dispersion produced by Daikin Industries, LTD. (D1F) for about 5 to 10 seconds and was subsequently dried at the normal temperature. This process was repeated two or three times. Thereafter, PTFE was applied onto the surface of the stainless steel wire. Thus, a unified structure of the stainless steel wire and the PTFE porous membrane was prepared in the same manner as in Example 2 except for the above-described processes.

In the tubular composite structure thus obtained, the respective PTFE porous membrane layers were united by fusion bonding through the gaps between the stainless steel wires. In addition, it was confirmed that the PTFE porous membrane layers were integrated in close contact along the surfaces of the respective stainless steel wires in a manner such that the wires were wrapped therewith. The reinforcement drawing strength of the composite structure was improved to 520±53 gf.

Example 5

The surface of a hard stainless steel wire having a length of 60 mm (the outer diameter: 0.30 mm) was roughened by rubbing with a paper file of No. 1500. Then, the stainless steel wire was immersed in a FEP dispersion produced by Daikin Industries, LTD. (ND1E) for about 5 to 10 seconds and was subsequently dried at the normal temperature. This process was repeated two or three times. Thereafter, PTFE was applied onto the surface of the stainless steel wire. Thus, a unified structure of the stainless steel wire and the PTFE porous membrane was prepared in the same manner as in Example 2 except for the above-described processes.

In the tubular composite structure thus obtained, the respective PTFE porous membrane layers were united by fusion bonding through the gaps between the stainless steel wires. Also, it was confirmed that the PTFE porous membrane layers were integrated in close contact along the surfaces of the respective stainless steel wires in a manner such that the wires were wrapped therewith. The reinforcement drawing strength of the composite structure was improved to 930±31 gf.

Example 6

The surface of a hard stainless steel wire having a length of 60 mm (the outer diameter: 0.30 mm) was roughened by rubbing with a paper file of No. 1500. A PTFE dispersion made by Daikin Industries, LTD. (D1F) was applied with a brush on a surface (the surface on the bonding side) of a sintered PTFE porous membrane [trade name: HP020-30, supplied from Sumitomo Electric Industries, Ltd., and having a thickness of 30 µm, a pore size of 0.2 µm, and a porosity of 60%], and it was subsequently dried at the normal temperature. A unified structure of the stainless steel wire and the PTFE porous membrane was prepared in the same manner as in Example 2 except that the above-described materials were used.

In the tubular composite structure thus obtained, the respective PTFE porous membrane layers were united by fusion bonding through the gaps between the stainless steel wires. Also, it was confirmed that the PTFE porous membrane layers were integrated in close contact along the surfaces of the respective stainless steel wires in a manner such that the wires were wrapped therewith. As a result of observing the adhered interfaces in detail, it was found that the adhesive (DIF) infiltrated into a PTFE porous membrane slightly, whereby a thin nonporous layer having a thickness of 5 µm or less was formed. The reinforcement drawing strength of the composite structure was 201±59 gf.

Example 7

The surface of a hard stainless steel wire having a length of 60 mm (the outer diameter: 0.30 mm) was roughened by rubbing with a paper file of No. 1500. A FEP dispersion produced by Daikin Industries, LTD. (ND1E) was applied with a brush on a surface (on the bonding side) of a sintered PTFE porous membrane [trade name: HP020-30, supplied from Sumitomo Electric Industries, Ltd.], and it was subsequently dried at the normal temperature. A unified structure of the stainless steel wire and the PTFE porous membrane was prepared in the same manner as in Example 2 except that the above-described materials were used.

In the tubular composite structure thus obtained, the respective PTFE porous membrane layers were united by fusion bonding through the gaps between the stainless steel wires. Also, it was confirmed that the PTFE porous membrane layers were integrated in close contact along the surfaces of the respective stainless steel wires in a manner such that the wires were wrapped therewith. Moreover, as a result of observing the adhered interfaces in detail, it was found that the adhesive (NDIF) infiltrated into a PTFE porous membrane slightly, whereby a thin nonporous layer having a thickness of 10 µm or less was formed. The reinforcement drawing strength of the composite structure was improved to 4266±537 gf.

Example 8

The surface of a hard stainless steel wire (the outer diameter: 0.30 mm) was roughened with a paper file of No. 1500. Subsequently, the stainless steel wire was formed into a tape-like configuration having a width of 1 cm by bending in a crimp pattern in such a manner as to trace a side of an isosceles triangle (FIG. 12). The tape-like structure thus prepared was sandwiched between PTFE porous tapes (DIF was applied on a bonding surface thereof as in Example 6) and the resultant product was put in a hot-blast circulated thermostatic vessel, which was set to have a temperature of 340° C. while a pressure of 3.1 kPa was applied, and was left under such conditions for 1 hour. Thus, a tape-like PTFE porous material (the width: 15 mm, the length: 30 cm) including the framework structural member of crimp pattern was prepared.

As shown in FIG. 13, the tape thus prepared was lapped spirally around the circumferential surface of a mandrel having an outer diameter of 20 mm, which was made by spirally winding a stainless steel board having a thickness of 0.1 mm and a width of 15 mm into a tubular form. The tape lapped around the mandrel was put in a hot-blast circulated thermostatic vessel which was set to have a temperature of 340° C. and the tape lapped around the mandrel was left under such conditions for 1 hour, and thereby it was formed into a tubular shape. In this way, a tubular composite structure having a framework structural member that can radially expand/shrink was produced.

From Example 8 it is understood that a stent-graft can be made simply and at low cost by using a tape-like (ribbon-shaped) composite structure.

Comparative Example 1

A stainless steel wire having an outer diameter of 0.25 mm was braided at a pitch of 3 mm into a lattice-like network (a square form having a lateral length of 100 mm), which was subsequently placed between two unsintered PTFE porous membrane sheets [trade name: UP020-80, supplied from Sumitomo Electric Industries, Ltd., having a pore size of 0.2 µm, and square form of 100 mm in lateral length]. The product thus prepared was placed between stainless steel boards each having a thickness of 1 mm, and was left for 2 hours at 340° C. while pressure of 6.2 kPa was applied thereon by placing a weight on the stainless steel board. After such heat treatment, it was found that the respective members were not bonded together and were separated from each other.

That is, since the intermediate composite material was subjected to a pressured heat treatment in a state in which it was sandwiched between the stainless steel boards, the respective PTFE porous membrane layers could neither be bonded together through the gaps of the stainless steel network nor be bonded with the stainless steel wires in such a manner as to achieve close contact along the surfaces of the respective wires so as to wrap the wires therewith. By comparing the results of Example 1 and those of Comparative Example 1, it can be understood that the method of the present invention is remarkably effective for making a composite structure of the PTFE porous membrane and a complicated framework structural member.

Comparative Example 2

First, as in Example 2, a mandrel having an outer diameter of 20 mm was prepared by spirally winding a stainless steel board having a thickness of 0.1 mm and a width of 15 mm into a tubular form. And, an unsintered PTFE porous membrane sheet having a width of 60 mm [trade name: UP020-80, made by Sumitomo Electric Industries, Ltd., the thickness: 80 µm, and the pore size: 0.2 µm] was lapped around the circumferential surface of the mandrel so as to form a two layered configuration sandwiching five hard stainless steel wires each having a length of 60 mm (Japanese Industrial Standard SUS304, the outer diameter: 0.30 mm). In this case, the hard stainless steel wires were arranged axially in parallel and with intervals at a pitch of about 10 mm.

Subsequently, the unsintered PTFE porous membrane sheet lapped around the mandrel was covered with an aluminum foil having a thickness of 50 µm, and furthermore an unsintered PTFE porous tape [a PTFE seal tape made by Nichias Corp., TOMBO 09082, the thickness: 0.1 mm] was tightly lapped spirally around it in 5 layers or more. This was subjected to heat treatment by being left for 2 hours in a hot-blast circulated thermostatic vessel the temperature of which was set to 340° C., and thereafter, the aluminum foil, the seal tape, and the mandrel were removed. Thus, a composite structure comprising the stainless steel wire and the PTFE porous membrane was prepared.

The composite structure thus obtained did not have such a configuration in which the PTFE porous membrane layers were bonded closely along the surfaces of the stainless steel wires so as to wrap the wires. The reinforcement drawing strength of this composite structure was only 0.9±0.6 gf. As a result of comparison between Example 2 and Comparative Example 2, it is understood that the method of the present invention makes it possible to manufacture a composite structure which has a superior mechanical strength and durability, exhibiting high reinforcement drawing strength of the metal wire.

Comparative Example 3

A hard stainless steel wire having a length of 60 mm (the outer diameter: 0.30 mm) was immersed in a FEP dispersion produced by Daikin Industries, LTD. (ND1E) for about 5 to 10 seconds and was subsequently dried at the normal temperature. Such process was repeated two or three times. Thereafter, PTFE was applied onto the surface of the stainless steel wire. A unified structure of the stainless steel wire and the PTFE porous membrane was prepared as in Comparative Example 2 except for the above-described processes. The composite structure thus obtained did not have such a configuration in which the PTFE porous membrane layers were bonded closely along the surfaces of the stainless steel wires so as to wrap the wires. The reinforcement drawing strength of this composite structure was 271±67 gf, which was a low value as compared with 930±31 gf of the corresponding composite structure prepared in Example 5.

Comparative Example 4

The surface of a hard stainless steel wire having a length of 60 mm (the outer diameter: 0.30 mm) was roughened by rubbing with a paper file of No. 1500. A FEP dispersion produced by Daikin Industries, LTD. (ND1E) was applied with a brush on a surface (on the bonding side) of a sintered PTFE porous membrane [trade name: HP020-30, supplied from Sumitomo Electric Industries, Ltd.], and it was subsequently dried at the normal temperature. A unified structure of the stainless steel wire and the PTFE porous membrane was prepared in the same manner as in Comparative Example 2 except that the above-described materials were used. The composite structure thus obtained did not have such a configuration in which the PTFE porous membrane layers were bonded closely along the surfaces of the stainless steel wires so as to wrap the wires. The reinforcement drawing strength of this composite structure was 1147±62 gf, which was a low value as compared with 4266±537 gf of the corresponding composite structure prepared in Example 7.

The invention claimed is:

1. A method of manufacturing a composite structure comprising a first polytetrafluoroethylene (PTFE) porous layer, a second PTFE porous layer, and a framework structural member having a plurality of gaps or openings, wherein the method includes the following Steps 1 through 3:

Step 1 for preparing an intermediate composite material which is formed by arranging the first PTFE porous layer, the framework structural member, and the second PTFE porous layer in this order and placing on and around a circumferencial surface of a mandrel Step 2 for applying pressure at least from one outside of the first and second PTFE porous layers through a mass of fine particles so that the first and second PTFE porous layers can be adhered not only with each other through the gaps or openings of the framework structural member, but also with the framework structural member closely along the surfaces of the respective elements of the framework structural member in such a manner as to wrap the respective elements; and Step 3 for uniting the respective adhered parts by heating at a temperature lower than the pyrolysis temperature of polytetrafluoroethylene in a state where pressure is applied, wherein:

in the Step 1, the framework structural member is sandwiched through fluoroplastics between the first and second PTFE porous layers, and thereby, in the Step 3, the first and second PTFE porous layers are united with the framework structural member through fluoroplastics closely along the surfaces of respective constituent elements of the framework structural member, the mandrel is made by lapping a plate spirally into a tubular form, a diameter of fine particles is 5 to 500 µm, the fine particles are at least one selected from the group consisting of aluminum oxide, calcium carbonate, silica, kaolin, clay, titanium oxide, zinc oxide, barium sulfate, magnesium hydrate, sodium chloride, or potassium chloride, and in the Step 1, a dispersion of the fluoroplastics is applied on a bonding surface of at least one of the first and second PTFE porous layers so that a nonporous layer having a thickness of 10 µm or less is formed.

2. The method of manufacturing a composite structure according to claim 1, wherein the mass of fine particles do not change in their form under the heat treatment at a temperature lower than the pyrolysis temperature of polytetrafluoroethylene.

3. The method of manufacturing a composite structure according to claim 1, wherein in Step 2, the intermediate composite material is placed in the mass of fine particles, and pressure is applied at least from one outside of the porous polytetrafluoroethylene layers through the mass of fine particles on which the pressure is applied from the outside.

4. The method of manufacturing a composite structure according to claim 1, wherein:

in Step 1, the intermediate composite material, in which the first PTFE porous layer, the framework structural member, and the second PTFE porous layer are arranged in the enumerated order, is placed on and around a circumferential surface of a cylindrical support block, and in Step 2, in a state in which the intermediate composite material is placed on the circumferential surface of the cylindrical support block, pressure is applied from the outer surface of the second PTFE porous layer through the mass of fine particles.

5. The method of manufacturing a composite structure according to claim 1, wherein the constituent element of the framework structural member is an elastic wire.

6. The method of manufacturing a composite structure according to claim 5, wherein the framework structural member is a tubular structure.

7. The method of manufacturing a composite structure according to claim 6, wherein the tubular structure is structured so as to be radially expandable/shrinkable.

8. The method of manufacturing a composite structure according to claim 5,
wherein the elastic wire is a metal wire.

* * * * *